United States Patent [19]

Fox

[11] Patent Number: 4,787,888

[45] Date of Patent: Nov. 29, 1988

[54] DISPOSABLE PIEZOELECTRIC POLYMER BANDAGE FOR PERCUTANEOUS DELIVERY OF DRUGS AND METHOD FOR SUCH PERCUTANEOUS DELIVERY (A)

[75] Inventor: Martin D. Fox, Storrs, Conn.

[73] Assignee: University of Connecticut, Storrs, Conn.

[21] Appl. No.: 56,471

[22] Filed: Jun. 1, 1987

[51] Int. Cl.[4] .................................... A61M 37/00
[52] U.S. Cl. ...................... 604/20; 604/304; 604/892.1; 128/24 A
[58] Field of Search .............. 604/20, 22, 890, 896, 604/897, 304, 305, 307; 128/24 A, 421, 798, 804

[56] References Cited

U.S. PATENT DOCUMENTS

| | | |
|---|---|---|
| 2,784,715 | 3/1953 | Kestler . |
| 3,358,677 | 10/1964 | Sheldon . |
| 3,742,951 | 7/1973 | Zaffaroni . |
| 3,814,097 | 6/1974 | Ganderton et al. . |
| 3,867,929 | 2/1975 | Joyner et al. . |
| 4,060,084 | 11/1977 | Chandrasekaran et al. . |
| 4,286,592 | 9/1981 | Chandrasekaran . |
| 4,309,989 | 1/1982 | Fahim . |
| 4,372,296 | 2/1983 | Fahim . |
| 4,460,372 | 7/1984 | Campbell et al. . |
| 4,474,570 | 10/1984 | Ariura et al. . |
| 4,486,194 | 12/1984 | Ferrara . |
| 4,557,723 | 12/1985 | Sibalis . |
| 4,573,996 | 3/1986 | Kwiatek et al. . |
| 4,614,178 | 9/1986 | Harlt et al. ............ 128/24 A |

FOREIGN PATENT DOCUMENTS

| | | | |
|---|---|---|---|
| 910466 | 7/1949 | Fed. Rep. of Germany ... | 128/24 A |
| 2756460 | 6/1979 | Fed. Rep. of Germany ........ | 604/20 |
| 3008975 | 9/1981 | Fed. Rep. of Germany ... | 128/24 A |
| 850079 | 7/1981 | U.S.S.R. ......................... | 128/24 A |
| 878268 | 11/1981 | U.S.S.R. ......................... | 128/24 A |
| 897252 | 1/1982 | U.S.S.R. ......................... | 128/24 A |

OTHER PUBLICATIONS

McElnay et al., "The Effect of Ultrasound on the Percutaneous Absorption of Lignocane," *British Journal of Clinical Pharmac* 1985, 20, pp. 421–424.

*Primary Examiner*—C. Fred Rosenbaum
*Assistant Examiner*—Ralph Lewis

[57] ABSTRACT

A bandage assembly for percutaneous administration of a medicament generates sonic vibrations to produce sonophoresis. The assembly has a bandage member with a cavity containing a medicament and having a piezoelectric polymer element extending thereacross. An sonic generator is coupled to the piezoelectric polymer element to supply it with energy to produce sonic vibrations perpendicular to the skin to drive the medicament into the pores. A second piezoelectric polymer element may surround the cavity to generate vibrations parallel to the skin to stretch the pores.

24 Claims, 3 Drawing Sheets

DISPOSABLE PIEZOELECTRIC POLYMER BANDAGE FOR PERCUTANEOUS DELIVERY OF DRUGS AND METHOD FOR SUCH PERCUTANEOUS DELIVERY (A)

BACKGROUND OF THE INVENTION

Phonophoresis (also known as sonophoresis or ultrasonophoresis) is the movement of a medicament through the skin by the application of sonic radiation to the medicament placed upon the skin. Although the technique has been well known in the field of physical therapy for some time, widespread application has been hindered by the requirement for supervision during the application of the ultrasonic radiation, and by the use of relatively large physical therapy machines for the application of that radiation Recently developed polymeric materials exhibiting piezoelectric properties now make possible a new generation of phonophoretic applicators which bypass any of the problems inherent in drug delivery using conventional transducers. Of these polymers, polyvinylidene fluoride (PVDF) is most readily available, but there are other polymeric materials which exhibit piezoelectric effects, and hybrid ceramic compositions in a polymer matrix have the characteristic of being flexible rather than brittle, and in quantity are much less expensive than conventional piezoceramics In addition to drug delivery, another broad application area for ultrasonics is in improved wound healing, because it has been well established that ultrasound by itself can speed up the healing process in open wounds Finally, not only can piezoelectric polymeric materials enhance drug delivery by conventional phonophoretic techniques, but also they can present the potential for totally new applications of sonic energy in improved drug delivery and sound heating. The large coupling between thickness and longitudinal modes ($d_{31}$) in such piezoelectric polymers, combined with the ability to make very long, thin elements from them, provides the opportunity to create bandages which can act upon the skin in new ways.

The present invention relates to bandage assemblies for phonophoresis of medicaments, and, more particularly, to a bandage assembly having piezoelectric components which contains a medicament to be phonophoretically transferred into a patient upon which it is placed.

in the broadest sense, the bandage provides a means for application of sonic energy to the skin by means of nonconventional polymeric sonic generators. The sonic energy may be applied in the conventional way, using the piezoelectric generator in the thickness mode, and it may also be applied as a stretching of the skin by driving the polymer in a thickness-longitudinal mode or it may be applied by a bimorph bender. It may be applied by a combination of the preceding depending on the type of medicament, the type of skin and the frequencies employed. The different elements that make up the sonic generator may be activated either at a single frequency, or at multiple frequencies applied simultaneously. The sonic energy may be applied either in continuous wave mode or in a burst mode.

Accordingly, it is an object of the present invention to provide a novel bandage assembly using piezoelectric polymers for percutaneous administration of medicaments.

It is also an object to provide such a bandage assembly which may be readily fabricated and which can utilize the sonic vibrations to stretch the skin as well as to drive the medicament therethrough.

Another object is to provide such an assembly in which the assembly may be utilized over an extended period of time to effect intermittent, or controlled rate, administration of the medicament.

A further object is to provide such an assembly which utilizes a compact and self-contained sonic generator which may be readily coupled to disposable bandage members.

SUMMARY OF THE INVENTION

It has now been found that the foregoing and related objects can be readily attained in a bandage assembly for percutaneous administration of a medicament. This assembly includes a bandage member having a cavity functionally opening on one surface thereof and a body element extending over the cavity and fabricated from a piezoelectric polymer. The bandage member has one surface adapted to be placed against the skin, and it has a medicament composition in the cavity. A pair of electrical contacts on the body element are disposed adjacent the opposite surfaces of the piezoelectric body element, and are connected to an sonic generator to generate sonic vibrations in the body element to induce percutaneous transfer of the medicament composition.

Preferably, the bandage member includes means for securing it to the skin of a user, and this is most conveniently an adhesive coating on the surface about the cavity. In its most desirable embodiment, the piezoelectric body element is fabricated as a bimorph from the piezoelectric polymer to generate sonic radiation perpendicular to the one surface, and the piezoelectric polymer is polyvinylidene fluoride.

Ideally, a additional portion of the bandage member is fabricated from a piezoelectric polymer and is connected to an sonic generator. The body element generates sonic vibrations perpendicular to the one surface or skin, and the additional piezoelectric portion generates vibrations parallel thereto. Preferably, this additional portion is annular and surrounds the cavity to effect stretching of the skin, and the bandage member has adhesive thereon about the cavity to secure it to the skin.

In the usual applications, the medicament composition comprises a medicament dispersed or dissolved in a carrier medium which is highly viscous.

Normally, the sonic generator includes a battery power source, a microprocessor and an oscillator. It preferably includes a switch for controlling the generation of the sonic vibrations, and the microprocessor controls the rate and frequency of the ultrasonic vibrations generated thereby.

In preparing and using the bandage for the percutaneous administration of medicaments, a bandage member is fabricated with a cavity functionally opening on one surface thereof and a body element of a piezoelectric polymer extends over the cavity. The bandage member has a surface adapted to be placed against the skin, and it has a pair of electrical contacts on the body element, one of which is disposed towards the skin surface and the other of which is disposed adjacent the opposite surface. A medicament composition is placed in the cavity, and the bandage member is secured with its surface against the skin of the user. A sonic generator is connected to the contacts, and the generator is operated to produce sonic vibrations of the body element to induce percutaneous transfer of the medicament composition.

In the preferred method, the body element vibrations are perpendicular to the one surface and the skin, and an additional piezoelectric portion generates vibrations parallel to the skin to effect stretching of the skin. Desirably, a microprocessor in the sonic generator is programmed to control the rate and frequency of the sonic vibrations generated thereby.

BRIEF DESCRIPTION OF THE ATTACHED DRAWING

DETAILED DESCRIPTION OF THE ILLUSTRATED EMBODIMENT

As indicated hereinbefore, the bandage assembly essentially includes a bandage member having a cavity functionally open on the surface thereof to be placed upon the skin and having a body element extending over the cavity and fabricated from a piezoelectric polymer. A pair of spaced electrical contacts extending from the body element provides the means for supplying the energy to produce sonic vibrations in the piezoelectric polymer from a sonic generator.

Although the bandage member may be formed integrally by molding or by machining a single piece of a piezoelectric polymer to provide the cavity and then affixing the contacts thereto, the preferred bandage members are assembled from plural components as is best seen in the attached drawings.

Figure 1:
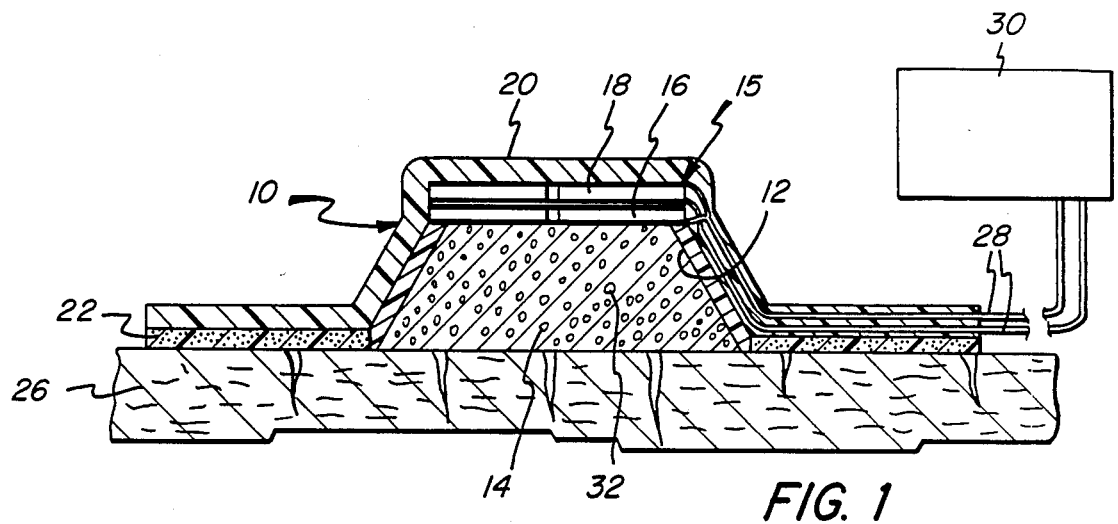
FIG. 1 is a schematic illustration of a bandage assembly embodying the present invention with the sonic generator schematically illustrated.

Turning first in detail to FIG. 1, therein illustrated is a bandage assembly including a bandage member generally designated by the numeral 10 and comprised of a frustoconical element 12 defining a chamber or cavity 14 therewithin. The piezoelectric polymeric body element 15 extends over the cavity 14 and is comprised of two superposed layers 16, 18, and a flexible cover element 20 provides the external surface and has an adhesive layer or coating 22 on its outwardly extending portions to secure the bandage member 10 to the skin 26 of the patient. Contacts or leads 28 extend from the piezoelectric layers 16, 18 outwardly of the cover element 20 to the sonic generator generally designated by the numeral 30.

Disposed within the cavity 14 is the medicament composition 32 which will be described more fully hereinafter. Conveniently, a layer of release paper (not shown) extends across the cavity 14 and is releasably engaged with the adhesive layer 22 to provide a temporary seal and closure prior to application to the patient's skin 26.

Figure 2:
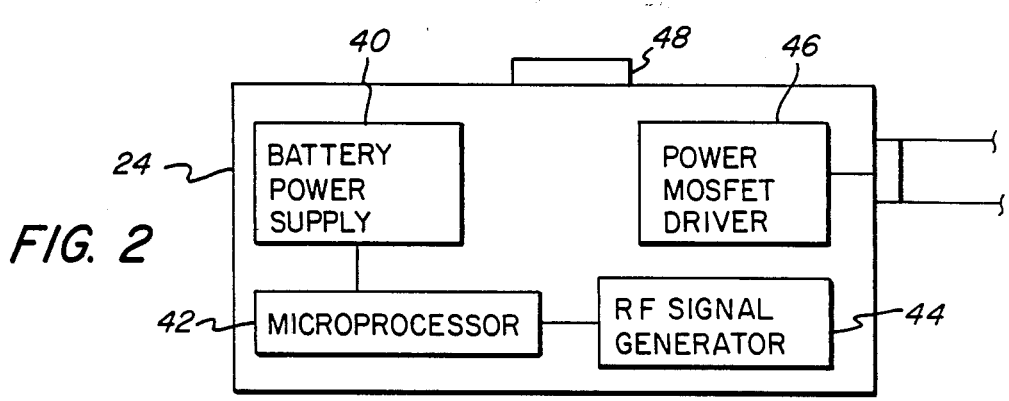
FIG. 2 is a schematic illustration of the components of the sonic generator.

In FIG. 2, the components of the sonic generator are schematically illustrated as comprising a housing 24 containing a battery power supply 40, a microprocessor 42, an RF signal generator 44, and a power MOSFET driver 46. A switch 48 is provided on the housing 24 to activate or deactivate the generator 30 manually. The operation of the components will be described more fully hereinafter.

Turning in detail first to the bandage element, the two layers 16, 18 of polymeric material are mounted in the bandage member 10 so that their directions of polarization both extend toward the surface of the skin 26, thus providing a two-layer stack with a primary resonance which is one-half that of either of the polymer layers separately. If commercially available polymer film of 110 micrometers thickness is used, the primary thickness mode resonance of this geometry will be about 5 MHz. The power output of such a composite stack compared to that of a single layer increases as the square of the number of layers, so the two layer stack illustrated in FIG. 1 will have four times the power output of a single layer at the same input voltage.

Turning in detail to the sonic generator 30, the battery power supply 40 is conveniently comprised of rechargeable cells such as nickel-cadmium, silver, and the like. The microprocesor controller 42 may be programmed with treatment regimens including total dosage and various pulse regimens which can be implemented in CMOS to conserve energy, and it may include an internal timer or be coupled to an auxiliary timer. The RF signal generator 44 is essentially an oscillator with frequency and burst duration controlled by the microprocessor 42. This may be implemented by using a voltage controlled oscillator (VCO) integrated circuit (not shown) and generating the control sequence from the microprocessor 32 by a digital to analog converter (DAC) chip (not shown). The final power output stage 46 can be implemented by a push-pull power amplifier fabricated using power MOS for high efficiency and simplicity of circuit design.

The medicament composition 32 is one in which the medicament is dissolved in a carrier vehicle, which should also be a transmitter of sonic energy and be reasonably viscous. Commercially available preparations include those designated "HEB Cream" by Barnes-Hind Co., and "Aquasonic Gel" by Parker Laboratories. HEB Cream is a combination of mineral oil, white petrolatum, stearyl alcohol, cetyl alcohol, sodium lauryl sulfate, methyl paraben and propyl paraben. Particular characteristics of the carrier may also aid in the phonophoretic process. Generally, the medicament will comprise 3–20 percent by weight of the carrier, depending upon the total dosage to be administered, and it should be either a liquid or soluble in the carrier medium.

Figure 3:
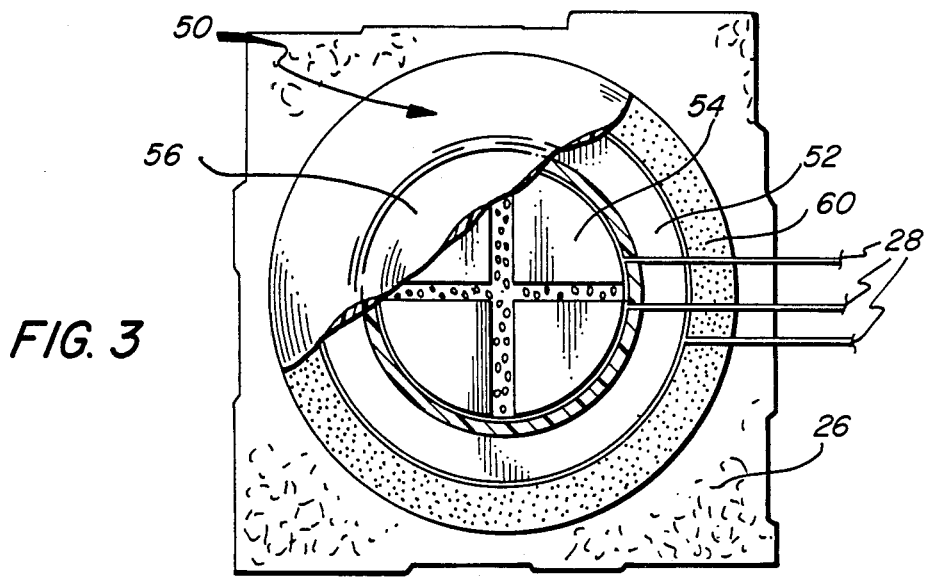
FIG. 3 is a schematic illustration in plan view of a preferred bandage member as applied to a fragmentarily illustrated skin area.
Figure 4:
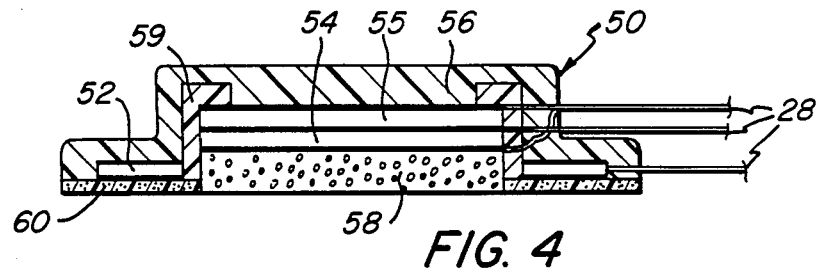
FIG. 4 is a schematic elevational view in section of the bandage member of FIG. 3.

Turning now to FIGS. 3 and 4, therein schematically illustrated is a preferred embodiment of the present invention with the cover partially removed for clarity of illustration. The bandage member generally designated by the numeral 50 includes an annular element 52 of the piezoelectric polymer operating in the thickness-longitudinal mode, and central layers or elements 54, 55 of piezoelectric polymers operating as bimorphs. A cover element 56 is superposed, and the medicament composition 58 is disposed in a cavity defined by the generally annular body 59 and central layers 54, 55. The adhesive layer 60 secures the bandage member 50 to the skin 26, and Leads 28 extend from the annular conductors (not shown) to the sonic generator (not shown).

Figure 5:
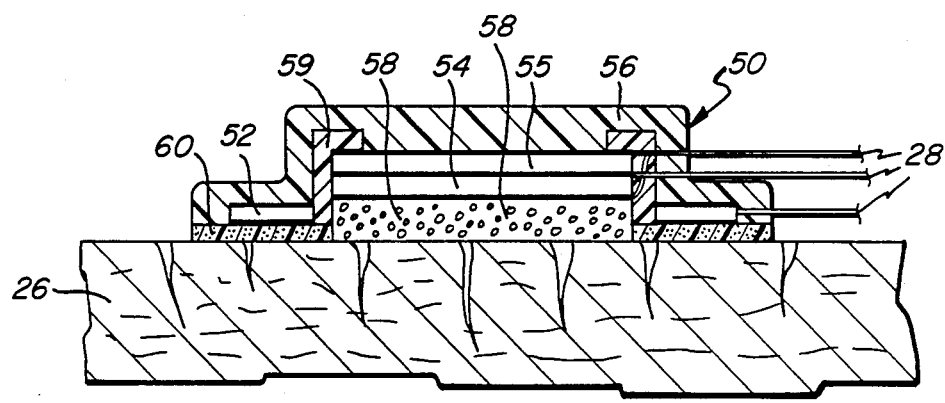
FIG. 5 is a similar view of the bandage showing pores and follicles of the skin.
Figure 6:
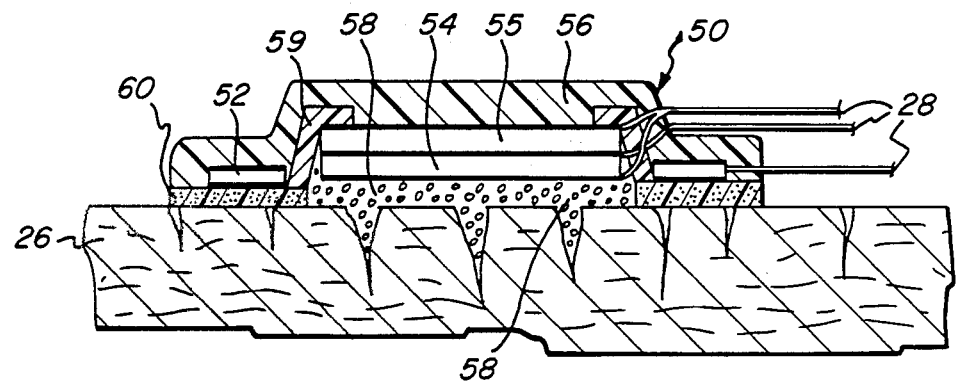
FIG. 6 is a view similar to FIG. 5 after stretching of the underlying skin by the sonic vibrations.

The basic concept of operation is illustrated in FIGS. 5 and 6, where a cross-section of the bandage member 50 is shown as superimposed on a region of human skin 26 or epithelium. The annular polymer element 52 pulls back and stretches the surface of the skin 26 while the bimorph elements 54, 55, operating in synchrony, drive the medicament downwardly and into the pores.

The leads are connected to the vertically spaced surfaces of the several piezoelectric elements. When a two layer structure is employed, one lead may be connected to the opposed faces, and a split lead may be connected to the upper and lower faces of the stack. In the instance of the structure shown in FIGS. 3 and 4, annular conductors may be placed in contact with the four elements of each layer, and the leads connected thereto.

This action creates a number of conditions favorable to the enhanced passage of medicament through the skin surface. Firstly, the medicament 58 is driven into the pores, which are lined by thin-walled cuboidal epithelial cells, rather than the cornified stratified squamous epithelium at the skin surface. Secondly, the flexure of the bimorph elements 54, 55 creates a positive pressure gradient which serves to drive the medicament 58 across the epithelial cell wall. Finally, the vibratory motion creates an agitation which promotes movement by diffusion along the concentration gradient by increasing the value of the partition coefficient in the diffusion equation that follows from Fick's First Law ($J = AK_p \Delta C/t$). In addition, a conventional thickness mode oscillation of the type effected by the bandage member in FIG. 1 can also be imposed simultaneously on the bimorph elements to create additional phonophoretic activity.

Figure 7:
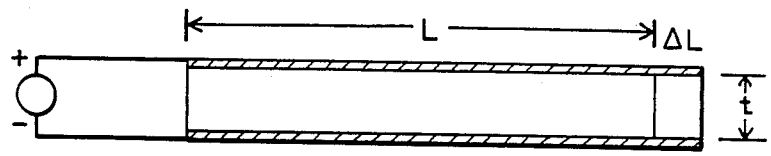
FIG. 7 is a schematic illustration of the method for the determination of the length expansion of a piezoelectric polymer to which sonic energy is applied.

Turning now to FIG. 7, therein is a schematic illustration of the method for estimating the change in length $\Delta L$ of a 1 cm long element of PVDF occurring in the longitudinal direction as a result of a 200 volt excitation applied in the thickness direction.

The change in length can be determined from the equation:

$$L = d_{31} V L / t$$

Calculating for $d_{31} = 23 \times 10^{-12}$ (m/m)(V/m), where V=200 volts, t=9 pm, L=1 cm, there is obtained a value of $L = 5.1$ μm. For an element of annular geometry, the stretch would be doubled in the central region of a 1 cm annulus to 10.2 μm.

Assuming that the pores consist of about 1 percent of the total surface area of the skin and that the stretching of the skin is distributed among the pores, which are long narrow invaginations as depicted in FIG. 5, the relative change in area will be $\pi(D+\Delta D)^2/\pi D^2$ or a 0.2 percent change in area for a 1 cm central region of the annular bandage structure. If this dimensional change is distributed among the pores, as is suggested by the geometry, the pore size would increase by 20 percent, a substantial increase.

Figure 8:
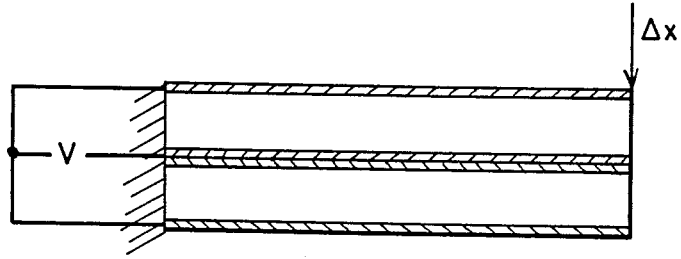
FIG. 8 is a schematic illustration of the method for the determination of the deflection of a bimorph assemblage of the piezoelectric polymer to which sonic energy is applied.

Turning now to FIG. 8, it is a schematic illustration used for estimating the degree of bending of a bimorph element by use of the equation:

$$x = 0.75 V d_{31} L^2 / t^2$$

Evaluating for an input voltage of 200 volts, a length of 0.5 cm, and a thickness of 28 μm, a deflection of 110 μm is determined to occur at the tip of the bender element. It should be noted that significantly greater deflections can be obtained by decreasing the thickness of the element.

Figure 9:
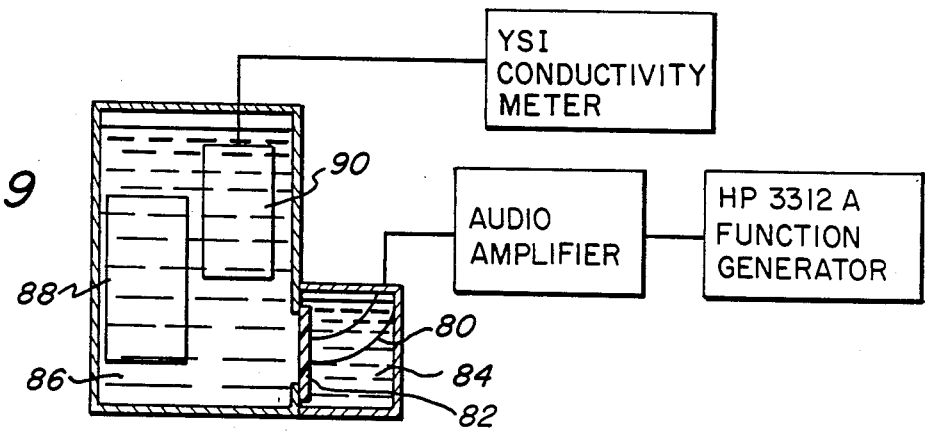
FIG. 9 is a schematic illustration of a test assembly for evaluating the effectiveness of transmission of a medicament through a membrane using a piezoelectric polymer bandage component.

In order to experimentally demonstrate the efficacy of the concepts of the present invention, an experimental test assembly was constructed as shown in FIG. 9.

A 28 μm thick PVDF piezoelectric polymer element 80 of about 2 cm in length was attached to a cellophane member 82 used to simulate skin for the purposes of this experiment. The PVDF element 8 was excited in the thickness-longitudinal mode by a continuous wave 1 kHz square wave of an amplitude of 24 volts peak to peak. The membrane was placed across an opening in the wall of a cell which was sealed by the membrane. On one side of the membrane was a solution 84 which contained 3 grams of acetylsalicylic acid in 100 ml. water; on the other was deionized water 86 in which were mounted the probe 90 of a conductivity meter and an acoustic absorber pad 88 to minimize reverberation.

The conductivity as measured by the Yellow Springs Instruments unit (YSI) has been shown to provide a monotonic indication of the concentration of acetylsalicylic acid (aspirin).

Figure 10:
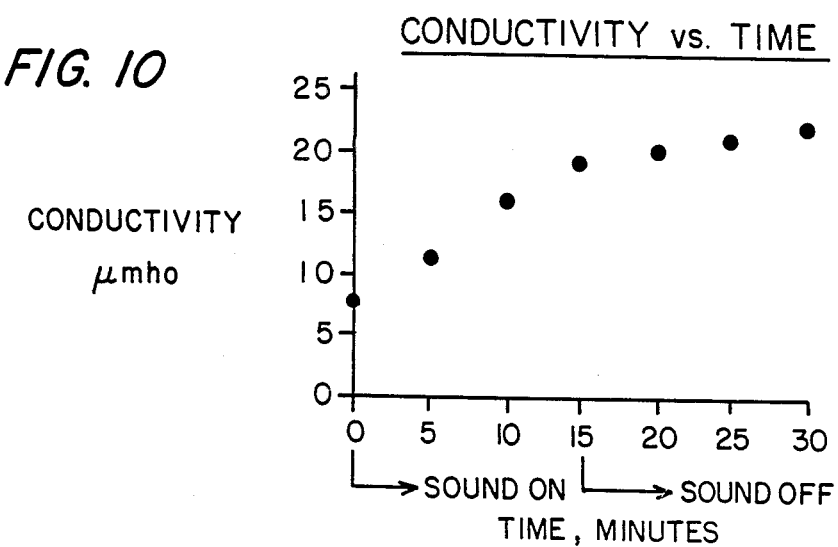
FIG. 10 is a graph of the results of the test in the assembly of FIG. 9.

The experimental procedure was to measure the conductivity of the receiver solution at 1 minute intervals. The conductivity change in the receiver was monitored for 15 minutes with the piezoelectric member generating sonic vibrations, and then for another 15 minutes with no sonic vibrations. The results are summarized graphically in FIG. 10.

The much slower rate of change of conductivity when the PVDF polymer is not generating ultrasonic vibrations should be noted. The conductivity change over 15 minutes with the polymer on was 11 μmho, while the conductivity change over 15 minutes with no vibration was 3 μmho. Thus, the phonophoretic effect apparently gave rise to a 366 percent increase in the rate of transport of aspirin in this experiment.

In the preferred embodiment seen in FIGS. 3 and 4, the cavity and the bimorph elements 54,55 may range from 1–5 cm. in diameter, and the annular element 52 may have a radial width of 0.2–1.0 cm. The peripheral portion of the adhesive element 60 should have a radial width of at least 0.2 cm., preferably at least 0.4 cm., to secure the assembly to the skin; a width in excess of 1.0 cm. serves no useful purpose. The cavity should have a depth of 1–20 mm., and the bimorph elements and annular element should have a thickness of about 30–110 micrometers.

The bandage assembly is preferably operated at voltage levels of 25–100 v. P-P, and at frequencies of 20 Hz to 2 KHz for the piezopolymeric materials.

Another embodiment that affords some additional advantages includes a piezoceramic disc of substantially smaller diameter than the bimorph elements seen in FIGS. 3 and 4 is (1–3 cm. diameter) spaced somewhat thereabove. In this instance, there will be obtained high frequency effects by having a second sonic generator generating a frequency in the range of 0.5-3 MHz to cause the ceramic element to deliver high frequency sonic vibrations.

The bandage members may be prefabricated and disposable. They can be filled with the medicament by the physician or patient in accordance with the instructions provided.

Thus, it can be seen from the foregoing detailed specification and attached drawings that the bandage member of the present invention provides a relatively simple and effective means for using phonopheresis to produce percutaneous delivery of a medicament. The bandage member can be readily fabricated utilizing piezoelectric polymers to produce vibrations normal to the skin of the wearer for inducing the transfer. Preferably it includes an additional piezoelectric polymer element generating vibrations parallel to the skin to cause the bandage member to stretch the skin and open the pores to improve the transfer. The sonic generator is readily coupled to the bandage member and may contain a microprocessor programmed as desired for the treatment regimen by use of EPROMs or the like.

Having thus described the invention, what is claimed is:

1. A bandage assembly for percutaneous administration of a medicament comprising:
    a. a bandage member having inner and outer surfaces and a cavity functionally opening on said inner surface thereof, said bandage member including a body element extending across said cavity adjacent said outer surface of said bandage member and fabricated from a piezoelectric polymer to generate vibrations perpendicularly to said inner surface, said bandage member having said inner surface adapted to be placed against the skin;
    b. a medicament composition in said cavity;
    c. electrical leads on said body element to supply energy thereto; and
    d. sonic generator means connected to said leads to generate sonic vibrations in said body element to induce percutaneous transfer of the medicament composition, said vibrations being within a frequency range of about 20 Hz to 2 kHz.

2. The bandage assembly in accordance with claim 1 wherein said bandage member includes means for securing it to the skin of a user.

3. The bandage assembly in accordance with claim 2 wherein said bandage member has an adhesive coating on said one surface thereof about said cavity to provide said securing means.

4. The bandage assembly in accordance with claim 1 wherein said body element includes two layers of piezoelectric polymer to produce a bimorph.

5. The bandage assembly in accordance with claim 1 wherein said piezoelectric polymer is polyvinylidene fluoride.

6. The bandage assembly in accordance with claim 1 wherein an additional portion of said bandage member surrounding said cavity is fabricated from a piezoelectric polymer connected to said generator means.

7. The bandage assembly in accordance with claim 6 wherein said additional portion generates vibrations parallel to said inner surface of said bandage member.

8. The bandage assembly in accordance with claim 6 wherein said additional portion surrounding said cavity is adopted to effect stretching of the skin.

9. The bandage assembly in accordance with claim 8 wherein said bandage member has adhesive thereon about said cavity to secure it to the skin.

10. The bandage assembly in accordance with claim 1 wherein said medicament composition includes a medicament dispersed in an ultrasonic medium.

11. The bandage assembly in accordance with claim 1 wherein said sonic generator includes a battery power source, a microprocessor and an oscillator.

12. The bandage assembly in accordance with claim 11 including a switch for controlling the generation of said sonic vibrations.

13. The bandage assembly in accordance with claim 11 wherein said microprocessor controls the rate and frequency of the sonic vibrations generated thereby.

14. The bandage assembly in accordance with claim 1 wherein said body element is a bimorph polymer and said bandage member includes an annular element of piezoelectric polymer extending about said cavity.

15. The bandage assembly in accordance with claim 1 wherein said bandage member includes a piezoceramic member spaced above said body element and coupled to a sonic generator means to generate high frequency sonic vibrations.

16. The bandage assembly in accordance with claim 15 wherein said sonic generator means includes means for supplying high frequency energy to said piezoceramic member.

17. In a method for the percutaneous administration of medicaments, the steps comprising:
    a. forming a bandage member having inner and outer surfaces and a cavity functionally opening on said inner surface thereof, such bandage member including a body element extending across said cavity adjacent said outer surface of said bandage member and fabricated from a piezoelectric polymer to generate vibrations perpendicular to said inner surface, said bandage member having said inner surface adapted to be placed against the skin and having electrical leads on said body element;
    b. placing a medicament composition in said cavity;
    c. securing said inner surface of said bandage member against the skin of the user;
    d. connecting sonic generator means to said leads; and
    e. operating said generator means to produce sonic vibrations of said body element to induce percutaneous transfer of said medicament composition, said vibrations being within a frequency range of 20 Hz to 2 KHz.

18. The method in accordance with claim 17 wherein said bandage member is adhesively engaged to the skin about said cavity.

19. The method in accordance with claim 17 wherein said piezoelectric polymer is polyvinylidene fluoride.

20. The method in accordance with claim 17 wherein said bandage member is fabricated with an additional portion of piezoelectric polymer disposed about said cavity and connected to said generator means.

21. The method in accordance with claim 20 wherein said additional portion generates vibrations parallel to said skin.

22. The method in accordance with claim 20 wherein said additional portion surrounds said cavity to effect stretching of the skin.

23. The method in accordance with claim 17 including the additional step of programming a microprocessor in said sonic generator to control the rate and frequency of the sonic vibrations generated thereby.

24. The method in accordance with claim 17 wherein said body element is formed as a bimorph and said bandage member is fabricated with an annular element of piezoelectric polymer extending about said cavity.

* * * * *